US006905230B2

(12) United States Patent
Schmitkons

(10) Patent No.: US 6,905,230 B2
(45) Date of Patent: Jun. 14, 2005

(54) UV LAMP RETAINER SYSTEM

(75) Inventor: James W. Schmitkons, Lorain, OH (US)

(73) Assignee: Nordson Corporation, Westlake, OH (US)

(*) Notice: Subject to any disclaimer, the term of this patent is extended or adjusted under 35 U.S.C. 154(b) by 134 days.

(21) Appl. No.: 10/643,170

(22) Filed: Aug. 18, 2003

(65) Prior Publication Data

US 2005/0040341 A1 Feb. 24, 2005

(51) Int. Cl.[7] .............................. F21K 7/00; A61N 5/00

(52) U.S. Cl. ....................... 362/263; 362/261; 362/257; 250/492.1; 313/113

(58) Field of Search ................................ 362/549, 548, 362/263, 257, 296, 306, 261, 433, 382; 250/492.1; 313/113, 318.01, 318.11, 318.12

(56) References Cited

U.S. PATENT DOCUMENTS

| | | | | |
|---|---|---|---|---|
| 5,060,125 A | | 10/1991 | Cowie et al. | 362/218 |
| 5,757,112 A | * | 5/1998 | Van Dulmen | 313/113 |
| 5,825,041 A | | 10/1998 | Belek et al. | 250/504 |
| 5,973,331 A | | 10/1999 | Stevens et al. | 250/492.1 |
| 6,265,830 B1 | | 7/2001 | Bretmersky et al. | 315/106 |
| 6,323,601 B1 | * | 11/2001 | Klein et al. | 313/113 |
| 6,457,846 B2 | | 10/2002 | Cook et al. | 362/321 |
| 6,520,663 B1 | | 2/2003 | Holmes et al. | 362/285 |

* cited by examiner

*Primary Examiner*—Sandra O'Shea
*Assistant Examiner*—Bao Q. Truong
(74) *Attorney, Agent, or Firm*—Wood, Herron & Evans, L.L.P.

(57) ABSTRACT

A lamp retainer for a UV lamp system includes a retainer bracket having a registration surface configured to engage a UV lamp to thereby facilitate accurate and repeatable positioning of the lamp in a lamp housing. The lamp retainer further comprises a retainer clip couplable to the retainer bracket and configured to bias a UV lamp toward the registration surface. The retainer clip facilitates removal and installation of the UV lamp in the lamp housing.

7 Claims, 2 Drawing Sheets

UV LAMP RETAINER SYSTEM

FIELD OF THE INVENTION

The present invention relates generally to ultraviolet (UV) curing systems, and more particularly to a retainer for supporting a UV lamp in a UV lamp system.

BACKGROUND OF THE INVENTION

UV cure systems are widely used in industry to cure inks, paints, adhesives and coatings by ultraviolet radiation. Several types of UV lamps systems are available. One commonly used system utilizes mercury arc lamps to generate the necessary ultraviolet radiation. These lamps generally comprise a quartz bulb containing an electrically excitable gas, such as mercury, sealed within the bulb. The bulb is sealed by insulating end caps which also contain electrodes for electrically exciting or ionizing the gas to create and sustain a high voltage arc. Mercury arc lamps are typically supported in a lamp assembly by spring clips, whereby the lamp may be easily removed and replaced as required. The clips are shaped to engage the lamp and to support it at a desired location within the lamp assembly. Mercury arc lamps are generally used with a reflector which helps to direct the UV energy emanating from the lamp to a substrate surface which is to be cured, dried, or otherwise affected by the energy.

In order to optimize curing efficiency, it is important to accurately position the mercury arc lamp with respect to the reflector and to the substrate. One drawback of prior UV lamps systems has been the difficulty associated with accurately positioning the bulb. Even when the bulb is initially installed in the correct position, the flexibility of supporting components often fail to maintain accurate positioning of the bulb, especially when exposed to the high heat generated by the UV lamp. This problem is particularly troublesome for lamp assemblies which are fabricated from sheet metal components. Accordingly, there is a need for a device for accurately positioning a UV lamp within a lamp assembly which overcomes drawbacks of the prior art such as those discussed above.

SUMMARY OF THE INVENTION

The present invention provides a lamp retainer that facilitates removal and installation of a UV lamp in a UV lamp system, to permit easy replacement of the UV lamp, while ensuring accurate and repeatable positioning of the lamp within a UV lamp housing. In one aspect of the invention, the lamp retainer includes a retainer bracket having a registration surface configured to engage a UV lamp and to provide a positive location for positioning the lamp with respect to the lamp housing and a reflector mounted within the housing. A retainer clip coupled to the bracket is configured to engage the lamp and bias the lamp toward the registration surface.

In an exemplary embodiment, the registration surface is defined by an aperture formed in the retainer bracket. The retainer clip is secured to the retainer bracket, adjacent the aperture. Opposing clip fingers of the retainer clip engage ceramic end caps of the lamp and urge the end caps into engagement with the registration surface.

In another aspect of the invention, a UV lamp system comprises a support member, a lamp reflector coupled to the support member, a lamp retainer, and a UV lamp. The lamp retainer includes a registration surface configured to ensure accurate positioning of the lamp with respect to the reflector, and a retainer clip for biasing the lamp into engagement with the registration surface.

These and other objects, advantages, and features of the invention will become more readily apparent to those of ordinary skill in the art upon review of the following detailed description of the preferred embodiments, taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
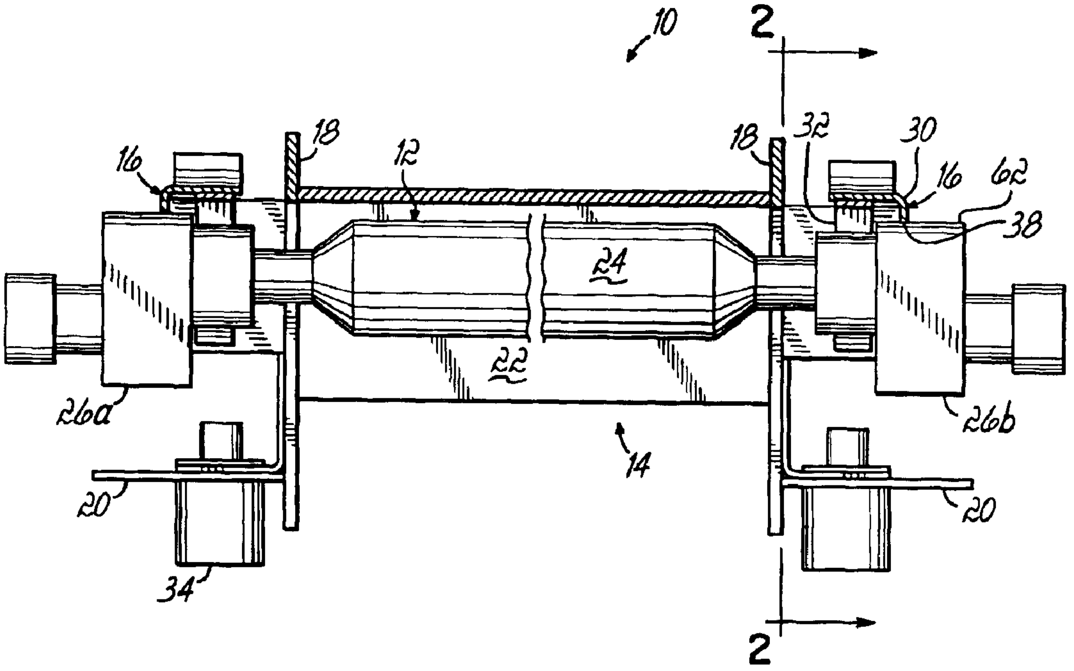
FIG. 1 is an elevation view of a UV lamp system including a lamp retainer according to the present invention.

Referring to FIG. 1, there is shown an exemplary UV lamp system 10 including a UV lamp 12 supported in a housing 14 by an exemplary retainer assembly 16 in accordance with principles of the present invention. The housing 14 is configured to receive and support the components of the lamp system 10. In the exemplary embodiment shown, the housing 14 includes spaced vertical housing walls 18 and laterally extending housing support members 20 disposed on oppositely facing sides of the vertical walls 18. A lamp reflector 22 is secured to the housing 14, generally between the vertical walls 18 and is configured to reflect UV light emanating from the lamp 12 and direct it toward a substrate material (not shown) to be cured, dried, or otherwise affected by the UV light. The lamp 12 comprises an elongate quartz glass bulb 24 sealed at its ends by ceramic end caps **26*a*, 26*b* and containing an electrically excitable gas therein. Electrodes (not shown) positioned at respective ends of the bulb 24 are supported by the ceramic end caps 26*a*, 26*b* and may be coupled to appropriate electrical connectors suitable for powering the lamp 12**.

The UV lamp 12 is supported within the housing 14 by a retainer assembly 16, comprising a retainer bracket 30 configured to define a positive registration feature that accurately positions the lamp 12, and a retainer clip 32 that engages the lamp 12 and retains the lamp 12 relative to the retainer bracket 30. Referring now to FIGS. 2–5, the lamp retainer 16 will be described in greater detail. The retainer bracket 30 is formed from sheet metal which has been stamped and punched to create an upstanding bracket member that may be secured to the lamp housing 14, for example, by fasteners 34.

Figure 4:
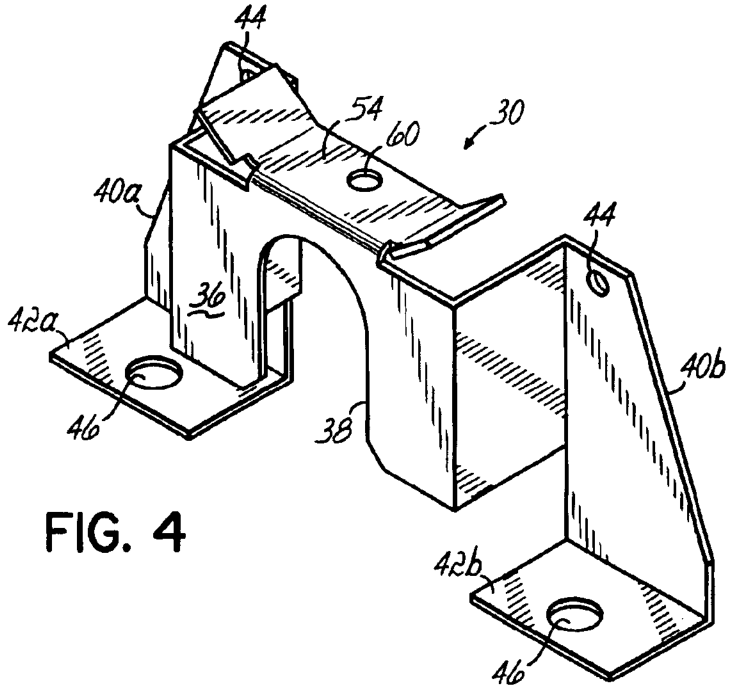
FIG. 4 is a perspective view of a support bracket of the retainer depicted in FIG. 3.

As best depicted in FIG. 4, the retainer bracket 30 includes a back wall 36 that forms a reference surface for accurately locating the lamp 12 within the lamp housing 14. In the exemplary embodiment shown, the reference surface is defined by an arcuately shaped aperture 38 formed in the back wall 36. The aperture 38 is configured to provide positive registration for the ceramic end caps 26 of the lamp 12, whereby the lamp 12 may be placed in engagement with the retainer bracket 30 to ensure accurate and repeatable positioning of the lamp 12 relative to the housing 14. First and second leg members 40*a*, 40*b* are disposed on opposing sides of the back wall 36. First and second foot members 42*a*, 42*b* extend from distal ends of the first and second leg members 40*a*, 40*b* and are configured to engage the laterally extending supports 20 of the housing 14 while the first and second leg members 40*a*, 40*b* register against the vertical housing wall 18. The retainer bracket 30 may thus be secured to the housing 14 by fasteners 34 installed through apertures 44, 46 formed in the leg members 40*a*, 40*b* and foot members 42*a*, 42*b* when placed in alignment with corresponding apertures formed in the housing 14 and arranged to position the reference surface aperture 38 of the bracket 30 at the desired location for receiving the UV lamp 12.

Figure 5:
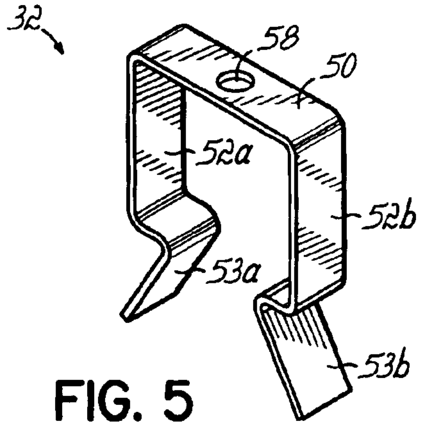
FIG. 5 is a perspective view of an exemplary clip of the lamp retainer depicted in FIG. 3.

As best illustrated in FIG. 5, the retainer clip 32 is formed from an elongate strip of flexible material, such as spring steel, to define a base portion 50 for engaging the retainer bracket 30, and first and second confronting clip fingers 52*a*, 52*b* configured to engage the ceramic end caps 26*a*, 26*b* of the lamp 12 therebetween. The distal ends 53*a*, 53*b* of the clip fingers 52*a*, 52*b* are angled outwardly to facilitate installation of the lamp end caps 26*a*, 26*b* within the clip 32. The clip 32 is coupled to the retainer bracket 30, such as by fastening the clip 32 to a support tab 54 formed in the retainer bracket 30 and extending from an upper end of the back wall 36. In the exemplary embodiment shown, clip 32 is fastened to support tab 54 by a fastener 56 installed through apertures 58, 60 formed in the clip 32 and support tab 54, respectively.

Figure 2:
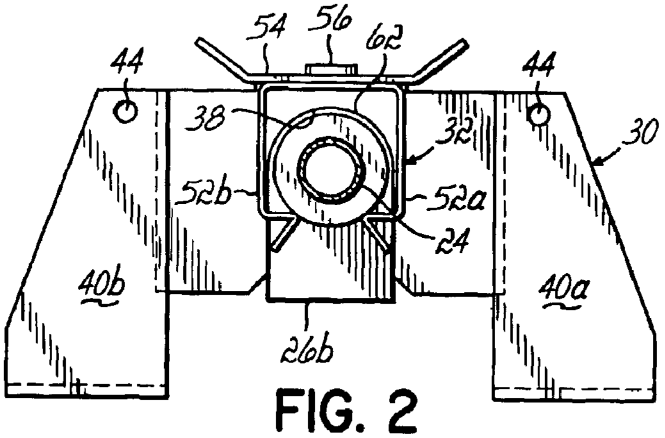
FIG. 2 is a cross-sectional view of the lamp system of FIG. 1, taken along line 2—2.
Figure 3:
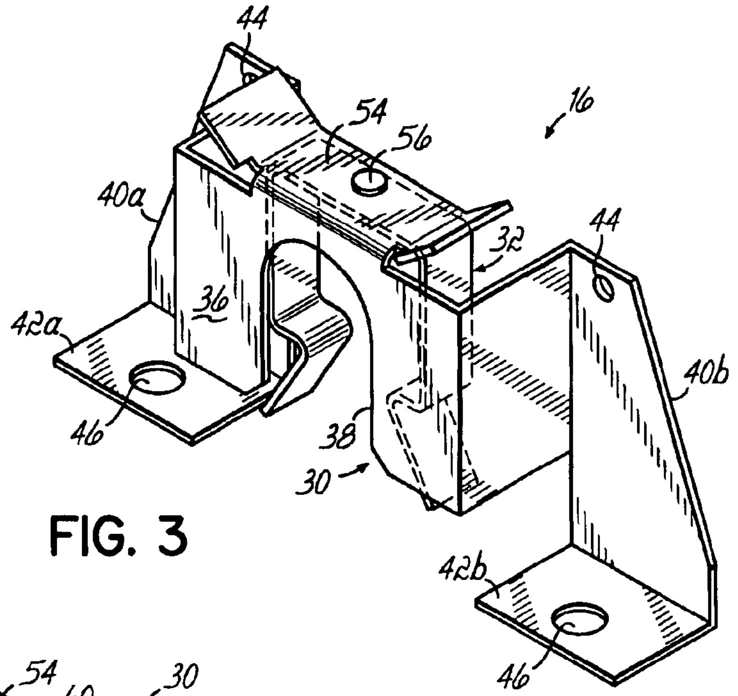
FIG. 3 is a perspective view of the exemplary lamp retainer of FIGS. 1–2.

Advantageously, the clip 32 is coupled to the bracket 30 adjacent the aperture formed in the back wall 36 such that when the ceramic end caps 26*a*, 26*b* of a UV lamp 12 are snapped into the clip 32, the clip fingers 52*a*, 52*b* bias the surface 62 of the end caps 26*a*, 26*b* into registration against the aperture 38 to accurately position the lamp 12 relative to the housing 14 and reflector 22, as shown in FIGS. 1 and 2. In the exemplary embodiment shown, the clip 32 is configured such that when the end caps 26*a*, 26*b* are snapped into the clip 32, the base portion 50 of the clip 32 is spaced from the end caps 26*a*, 26*b* and only the distal ends 53*a*, 53*b* of the clip fingers 52*a*, 52*b* engage the end caps 26*a*, 26*b* so that accurate positioning of the lamp 12 is controlled by the aperture 38.

The lamp retainer 16 of the present invention thus facilitates efficient installation and removal of a UV lamp 12 from a lamp assembly 10 while ensuring accurate and repeatable location of the lamp 12 with respect to the lamp housing 14, reflector 22. Advantageously, the positive registration feature of the lamp retainer 16 provides robust location performance that accommodates manufacturing variations in the retainer clip 32 or distortion that may occur in service. This robust performance also permits manufacturing tolerances to be loosened, thereby lowering manufacturing costs for the clip 32.

While the present invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope or spirit of the general inventive concept.

What is claimed is:

1. A UV lamp system comprising:

a housing;

a reflector mounted in said housing;

a UV lamp;

at least one retainer bracket coupled to said housing and having a registration surface which positions said UV lamp with respect to said reflector; and a retainer clip coupled to said retainer bracket and configured to engage said UV lamp and to bias said UV lamp against said registration surface.

2. The UV lamp system of claim 1, wherein said retainer bracket includes an aperture with an edge and said registration surface is defined by said edge.

3. The UV lamp system of claim 1, wherein said UV lamp includes an end cap and said registration surface is configured to engage said end cap.

4. The UV lamp system of claim 1, wherein said UV lamp includes at least one end cap having an outer surface, said outer surface contacting said registration surface of said retainer bracket when said retainer clip biases said lamp against said registration surface.

5. A UV lamp system comprising:

a housing;

a reflector mounted in said housing;

a UV lamp;

a retainer bracket formed from a single sheet of material, said retainer bracket coupled to said housing and having a slot defining a registration surface which positions said lamp with respect to said reflector; and a retainer clip coupled to said retainer bracket and configured to engage said UV lamp and to bias said UV lamp against said registration surface.

6. The UV lamp system of claim 5, wherein said retainer bracket comprises at least one leg member engaging said housing and positioning said registration surface for accurate location relative to the housing.

7. The UV lamp system of claim 5, wherein said retainer clip comprises a base portion and first and second confronting clip fingers extending from said base portion, said clip fingers having distal ends engaging said UV lamp such that said base portion is spaced from said lamp.

* * * * *